United States Patent [19]

Thompson

[11] Patent Number: 4,733,850

[45] Date of Patent: Mar. 29, 1988

[54] APPARATUS AND METHOD FOR ENABLING ATRAUMATIC PASSAGE OF A SEVERED TENDON THROUGH A TENDON SHEATH OR OTHER ENCLOSED SPACE

[76] Inventor: James S. Thompson, 112 Upnor Rd., Baltimore, Md. 21202

[21] Appl. No.: 4,662

[22] Filed: Jan. 20, 1987

[51] Int. Cl.[4] .................. A61F 13/00; A61B 17/00
[52] U.S. Cl. .................. 254/134.4; 128/303 R; 128/334 R; 128/346
[58] Field of Search .......... 128/334 R, 303 R, 346, 128/346; 623/13; 254/134.3 R, 134.4

[56] References Cited

U.S. PATENT DOCUMENTS

| | | | |
|---|---|---|---|
| 443,823 | 12/1890 | Cope | 254/134.4 |
| 526,141 | 9/1894 | Bloomer | 254/134.4 |
| 1,033,587 | 7/1912 | Hodgman | 254/134.4 |
| 1,035,994 | 8/1912 | Mueller | 254/134.4 |
| 2,287,257 | 6/1942 | Lear | 254/134.4 |
| 3,119,600 | 1/1964 | Bitter | 254/134.4 |
| 3,301,531 | 1/1967 | Corsiglia | 254/134.4 |
| 3,842,441 | 10/1974 | Kaiser | 623/13 |
| 4,596,381 | 6/1986 | Hamrick | 254/134.4 |

FOREIGN PATENT DOCUMENTS 0022593  2/1979  Japan ........................ 254/134.3 R

*Primary Examiner*—Richard C. Pinkham
*Assistant Examiner*—Gary Jackson
*Attorney, Agent, or Firm*—David M. Carter

[57] ABSTRACT

There is provided an apparatus for enabling the placement of a severed tendon to a position in its associated sheath to be repaired or passing a tendon end through any small enclosed space. The apparatus includes an elongated, flexible hollow tube with openings at both ends, and is received in the sheath. The tube has two sections with one section being somewhat rigid, although flexible, while the other section is thin, collapsible, and flares out. The flared section receives an end portion of the severed tendon. The opening in the end of the more rigid section is connected to a source of suction. The suction holds the tendon in place within the tube and causes the flared section to collapse tightly about the end portion of the tendon. The tube and the tendon are pulled through the sheath to the place where it was severed for repair. A specialized pair of forceps may be used to grip the tendon for placement in the flared section of the tube, and a specialized adapter may be used to connect the end of the more rigid section of the tube to the source of suction.

15 Claims, 10 Drawing Figures

APPARATUS AND METHOD FOR ENABLING ATRAUMATIC PASSAGE OF A SEVERED TENDON THROUGH A TENDON SHEATH OR OTHER ENCLOSED SPACE

BACKGROUND OF THE INVENTION

This invention relates to a means for threading a tendon end through an enclosed space. More particularly, it relates to a means for threading the end of a severed flexor tendon through its associated sheath in the hand.

Tendons which bend the human finger are called flexor tendons. Each finger has two flexor tendons, which arise from sublimis and profundus muscles in the forearm. The sublimis flexor divides into a Y and its distal ends are attached to a bone in the finger. The profundus flexor passes through the Y division of the sublimis and its distal end is attached to the most distal bone in the finger. For simplification, the flexor tendons in each finger will normally be referred to as a single tendon unless otherwise indicated. A simplified illustration of the flexor tendon in a finger is set forth in FIG. 1.

FIG. 1 shows the human finger 10 with parts of the skin and flesh removed. Flexor tendon 12 arises from muscles in the forearm 14 and is connected to bones 16 and 18 in the finger. The connection places to the bones are generally points 20, 22, and 24. Tendon 12 passes through substantially hollow tendon sheath 26 which includes a plurality of pulleys 28 through 32. The pulleys approximate the tendons close to the bones and when the finger is flexed the pulleys provide strong mechanical advantage for action of the flexor tendons on the bones in addition to preventing "bowstringing" of the flexor tendons away from the bones.

When the flexor tendon is severed because of a traumatic injury to the finger such as, for example, a deep cut, it has a tendency to retract out of the finger area into the palm area 13 because of muscle tension on the tendon end. A typical post trauma retracted, coiled up flexor tendon is shown in FIG. 3. In order for the surgeon to repair the tendon, it is necessary to thread the tendon back through the sheath. This has proved to be very difficult and almost impossible without doing damage to the tendon itself or the sheath, part of which is a thin membrane, and its fibrous pulleys. The problem is exacerbated when only one of the flexor tendons is severed, in particular the profundus tendon, whereby damage to the intact sublimis tendon must be avoided during re-threading.

Facilitation of tendon end passage through the sheath and other spaces, such as holes in the bone will speed surgical repair and reconstruction. Various methods have been utilized to attempt to thread the tendon back through the sheath. In one method, the free end of the tendon is sutured to one end of a solid silastic rod. The solid rod is passed through the sheath, pulling the tendon along through the sheath to the place of repair. However, it has been found that the end of the tendon quite often would bind up on the pulleys, causing damage to the tendon end, pulleys, or, in the case where only one of the tendons was severed, the intact tendon was damaged. Furthermore, the thin membrane part of the sheath was often damaged. The damage normally occurred because it is nearly impossible to abut the end of the tendon against the end of the rod without leaving an overhang of the tendon end or suture material, causing snags.

Rigid metal tendon passer rods which utilized teeth in jaws to grip the end of the tendon are also currently available. However, those metal rods are too rigid to readily pass through the sheath and the teeth often damage the tendon. Furthermore, the space required to open the jaws is not available in many circumstances.

In some cases, it has been proposed to totally replace the flexor tendon with a prosthesis, an example of which is disclosed in U.S. Pat. No. 3,613,120, issued to McFarland. However, such a radical approach to repairing a severed tendon is highly undesirable and has proven unsuccessful.

OBJECTS OF THE INVENTION

It is therefore one object of this invention to provide an improved apparatus for enabling the passage of tendon ends to the site of repair through the tendon sheath.

It is another object to provide an improved apparatus for enabling the passage of tendons through any anatomic structure, e.g., hole in bone or other tendon.

It is still another object to provide an improved apparatus for enabling the atraumatic passage of the flexor tendon, avoiding substantial damage to its associated sheath and pulleys.

SUMMARY OF THE INVENTION

In accordance with one form of this invention, there is provided an apparatus for enabling the placement of a severed tendon end to a position to be repaired. The apparatus includes an elongated hollow tube having first and second sections connected together and having openings at both ends. The first section of the tube is semi-rigid but flexible, while the second section of the tube is thin, flared out, and readily collapsible. The tube is placed in the sheath associated with the severed tendon. The first end of the tube is connected to a source of suction. A portion of the end of the tendon is initially received in the flared portion and the flared portion collapses about the severed end by the suction, thereby firmly holding the tendon to the tube. The tube and the tendon are pulled together through the tendon sheath. Suction is turned off, and the tendon is repaired without substantial trauma to itself, the tendon sheath, its pulleys, or any intact tendon. A specialized tool may be used for placing the end portion of the severed tendon in the flared section of the tube. Also, a specialized adapter may be connected between the rigid section of the tube and the source of suction. This apparatus may also be used for the atraumatic passage of tendons through any other small rigid anatomic spaces, especially holes in bone.

DESCRIPTION OF THE PREFERRED EMBODIMENT

Figure 4:
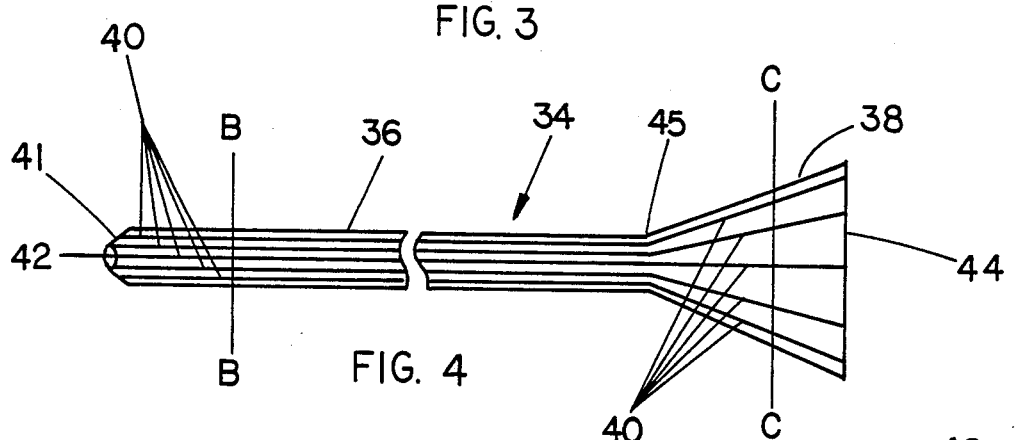
FIG. 4 is a partial side elevational view of the apparatus of the subject invention but being somewhat enlarged for clarification.

Referring now more particularly to FIG. 4, there is provided an elongated hollow tube 34 having a semi-rigid flexible end 36 with a uniform outer diameter and a thin flared collapsible end 38 having a non-uniform outer diameter. Tube 34 is preferably made of a silicone or other inert plastic material. A plurality of synthetic threads 40 are embedded in the plastic material of the tube and extend longitudinally from one opening 42 of the tube to the other opening 44. The threads enhance the tensile strength of the tube, particularly in the neck area 45 where the flared collapsible end 38 joins the semi-rigid flexible end 36.

Figure 5:
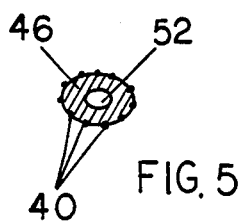
FIG. 5 is a sectional view of the apparatus of FIG. 4 taken through section lines B—B.

As can be seen in FIG. 5, the threads are evenly spaced about the periphery of the tube. The tube is somewhat oval shaped to conform somewhat to the shape of the tendon sheath 26.

Figure 1:
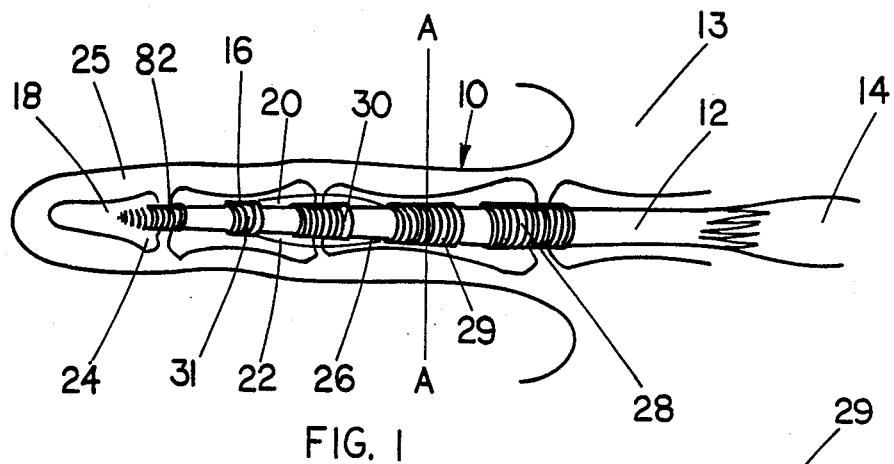
FIG. 1 is a simplified plan view of the human finger with portions of the skin and flesh removed showing the flexor tendon in place.
Figure 2:
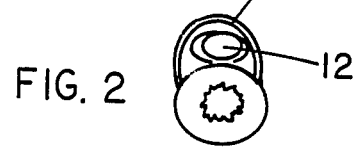
FIG. 2 is a sectional view of FIG. 1 taken through lines A—A.
Figure 3:
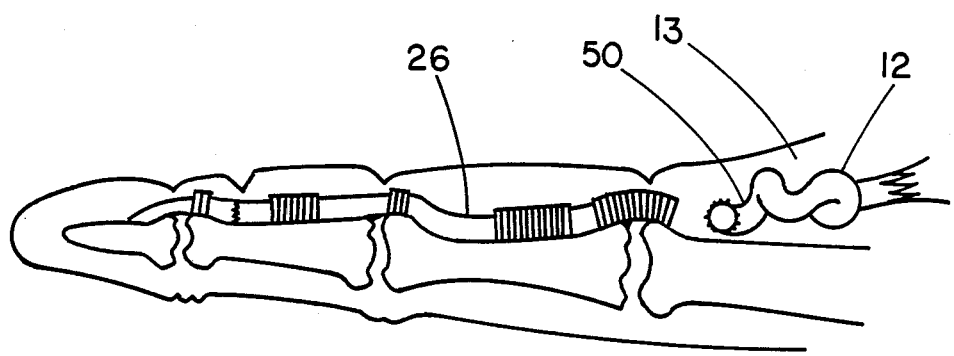
FIG. 3 is a side elevational sectional view of the finger shown in FIG. 1; however, with the flexor tendon having been severed.
Figure 6:
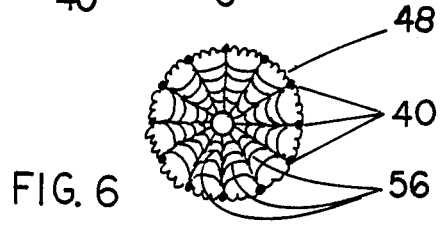
FIG. 6 is a sectional view of FIG. 4 taken through section lines C—C.

Again referring to FIG. 4, the end 41 of the tube is made tapered so that it is easily inserted and moved through tendon sheath 26 shown in FIG. 3. The flared end 38 is made substantially thinner than the tapered end 41. This may be more readily seen in comparing FIG. 5 to FIG. 6, whereby wall 46 is rather thick, while wall 48 is rather thin. The purpose of making wall 48 thin is so that flared section 38 may readily collapse onto the end portion 50 of severed tendon 12, shown in FIG. 3. The collapsed state of flared section 38 is better seen in reference to FIG. 8.

Figure 7:
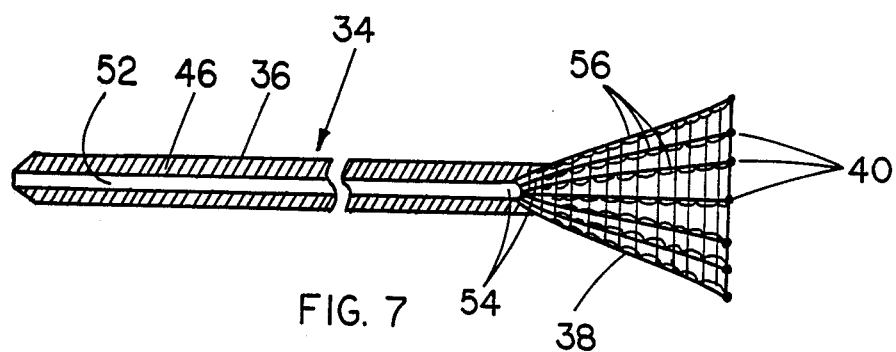
FIG. 7 is a sectional side elevational view of the apparatus of FIG. 4.

Referring now to FIG. 7, which is a sectional view of tube 34 of FIG. 4, it may be seen that tube 34 is hollow with somewhat round channel 52 extending through the semi-rigid flexible section of the tube to throat 54. Channel 52 should be smaller in diameter than tendon 12 so that the tendon will not pass into channel 52 in the thicker semi-rigid flexible part of the tube and so that the channel will become substantially sealed when suction is applied to opening 42. Preferably, flared section 38 includes a plurality of soft corrugations 56, extending into the interior of the flared section and creating an irregular concentric thin membranous surface for gripping the end 50 of the tendon.

Figure 8:
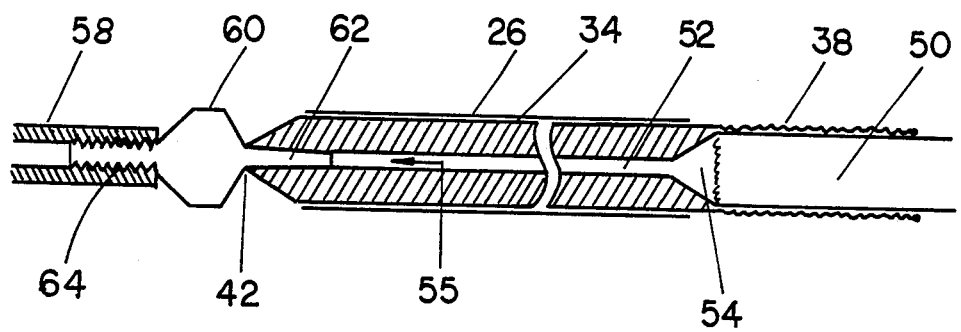
FIG. 8 is a sectional side elevational view of the apparatus of FIG. 7 having been threaded into a tendon sheath, however, with the flared portion having been collapsed about a severed tendon end after the semi-rigid, flexible section has been connected to a source of suction.

FIG. 8 shows the tube having been passed into tendon sheath 26 in the finger, the end 50 of tendon 12 having been placed into the flared section 38 and the suction connection having been made. Tube 34 is shown with the flared section 38 having been collapsed about tendon end 50. The collapsing occurs because of suction being supplied at opening 42 in the tube. A standard suction source (not shown) is connected to tube 58, which is made of smooth plastic. A specialized adapter or connector 60 is attached to tube 34 by placing needle nose 62 into opening 42. The opposite end of the special adapter includes a plurality of grooves 64 which engage and lock the smooth plastic suction tube 58 in place. With the application of suction, the longitudinal threads 40 and soft internal corrugations 56 hold the tendon tightly in the now collapsed section 38. The tube and thus the tendon is then pulled through the sheath 26 so that the tendon is in a position where the surgeon may reattach the tendon 12 to the bone or reattach the severed tendon ends.

Figure 9:
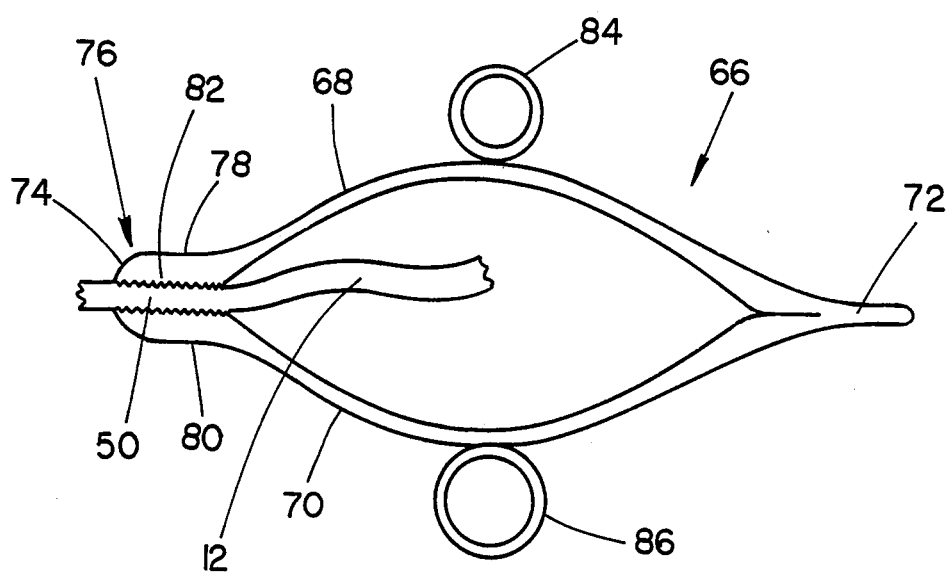
FIG. 9 is a side elevational view of a specialized tool for inserting the tendon into a portion of the apparatus of FIG. 7.
Figure 10:
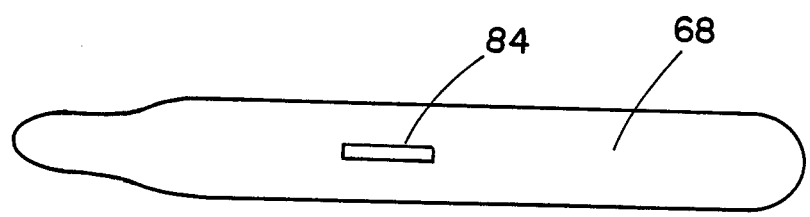
FIG. 10 is a top view of the apparatus of FIG. 9.

The end of portion 50 of tendon 12 may be placed into the flared out portion 38 by hand, but preferably by the use of a special tool shown in FIGS. 9 and 10, referred to as "Insertion Forceps". The Insertion Forceps 66 is preferably made of resilient metal or plastic, and includes a pair of arms 68 and 70 connected to one another at rear end 72. The forceps are spring biased to the neutrally closed position. The front end 74 of the forceps is tapered to better enable the insertion of the end portion 50 of severed tendon 12 into the flared section 38 of the tube. The end 76 is formed by a pair of jaws 78 and 80, each having a plurality of extremely fine delicate teeth 82 for gently grasping the tendon. The forceps also include a pair of finger rings 84 and 86 for enabling the user to more easily open the forceps and withdraw it from the flared end 38 after the tendon end 50 has been inserted.

The above described apparatus may be used by following the procedure set forth below:

The flexor tendon sheath 26 is exposed by the surgeon in the palm area 13 and in the finger area 25 near the place where the tendon was severed. The tapered end 41 of tubular member 34 is placed into the exposed portion of the sheath 26 in the palm area and threaded through inside of the sheath to the exposed portion of the sheath in the finger area with both ends of the tubular member extending out of the sheath. The needle nose 62 of adapter 60 is placed into opening 42 of the tube. The end portion 50 of severed tendon 12 is gently grasped by jaws 78 and 80 of forceps 66 and placed into flared section 38 of tube 34 in the position generally indicated in FIG. 8. Preferably, the end of the tendon contacts the throat region 54 of the flared out portion 38, as shown in FIG. 7 and FIG. 8. Suction is applied to channel 52 of the tube in the direction shown by the arrow 55, thus causing the flared section 38 to collapse about the tendon, grasping it with soft flexible material and sealing that end of the tube.

The tendon is firmly held in its position at throat 54 by the suction and by the grasping seal created by the collapsed flared portion 38, the friction of the filaments 40 against the tendon in the flared section, and the membraneous concentric corrugations 56.

With the suction remaining on, the tube, with the tendon connected thereto, is pulled through the sheath 26 toward the finger area 25 and completely out of the sheath. With the end 50 of tendon enclosed by the collapsed flared section 38, there is no place for the tendon to snag against a pulley, the remaining membrane portion of the sheath, or another tendon in the sheath, thereby avoiding the trauma and surgical delays which occurred using prior techniques.

Suction is turned off, and end 50 of the tendon is removed from the flared section 38 and the severed tendon is repaired or reinserted into bone. The above-described method would also be useful in passing tendon ends through any small rigid space, such as a hole in a bone.

From the foregoing description of the illustrative embodiment of this invention, it will be apparent that many modifications may be made therein. It will be understood, therefore, that the above described embodiment is intended as an exemplification of the invention only, and that the invention is not limited thereto. It is to be understood that it is intended that the appended claims cover all such modifications that shall fall within the true spirit and scope of the invention.

I claim:

1. An apparatus for enabling the placement of a severed tendon to a position to be repaired, comprising:
an elongated hollow tube having a first section and a second section connected together; said tube having openings at both ends; said first section of said tube being semi-rigid and flexible; said second section of said tube being flared and being readily collapsible; said first section of said tube adapted to be connected to a source of suction; a portion of the severed tendon adapted to be received inside said second section; the suction causing said second section to collapse about the tendon, whereby the tendon is firmly held in place in said collapsed second section; said tube being of a size so as to readily be received inside of a passage in the body.

2. An apparatus as set forth in claim 1, wherein said tube is somewhat oval shaped.

3. An apparatus as set forth in claim 1, wherein said first section of said tube has substantially thicker walls than the said second section.

4. An apparatus as set forth in claim 1, wherein said first section of said tube is somewhat tapered near its opening.

5. An apparatus as set forth in claim 1, further including at least one strength member in said tube.

6. An apparatus as set forth in claim 5, wherein at least one strength member includes a plurality of synthetic threads embedded in said tube and extending along the longitudinal axis thereof from said first end to said second end.

7. An apparatus as set forth in claim 1, further including a plurality of soft concentric corrugations extending from said second section of said tube towards its insides.

8. An apparatus as set forth in claim 1, further including an adapter connected to said opening in said first section.

9. An apparatus as set forth in claim 8, wherein said adapter includes an elongated needle nose extending into the hollow portion of said tube, said adapter being grooved for connection to a suction source.

10. An apparatus as set forth in claim 1, further including an instrument for placing a portion of said severed tendon into said second section of said tube, said instrument including a grasping means for holding said tendon.

11. An apparatus as set forth in claim 10, wherein said grasping means includes a pair of delicate jaws, said jaws each having atraumatic roughened surfaces.

12. An apparatus as set forth in claim 11, wherein said jaws are neutrally spring biased closed.

13. An apparatus as set forth in claim 11, wherein said instrument includes a pair of finger rings.

14. An apparatus as set forth in claim 11, wherein said jaws are rounded at one end.

15. An apparatus as set forth in claim 1, wherein said first section of said tube and said collapsed second section of said tube being of a size so as to readily be received inside of a flexor tendon sheath.

* * * * *